United States Patent [19]
Pequignot

[11] 3,939,844
[45] Feb. 24, 1976

[54] METHOD AND APPARATUS FOR STIMULATING A HEART TO ELIMINATE RHYTHMIC ABNORMALITIES, ESPECIALLY TACHYCARDIAS

[76] Inventor: Michel Pequignot, 14 Villa Desire Filleaud, 92140 Clamart, France

[22] Filed: Oct. 11, 1974

[21] Appl. No.: 514,263

[30] Foreign Application Priority Data
Oct. 18, 1973  France .............................. 73.37161

[52] U.S. Cl. ......................................... 128/419 PG
[51] Int. Cl.² ............................................. A61N 1/36
[58] Field of Search ...... 128/419 C, 419 DE, 419 P, 128/419 R, 421, 422, 423

[56] References Cited
UNITED STATES PATENTS
3,693,627  9/1972  Berkovits ...................... 128/419 PG OTHER PUBLICATIONS
Merx et al., "Medical and Biological Engineering," Vol. 10, No. 2, Mar., 1972, pp. 297-300.
Seimitt et al. "Medical Instrumentation," Vol. 7, No. 1, Jan. – Feb., 1973, p. 77, abstracts.

Primary Examiner—William E. Kamm
Attorney, Agent, or Firm—Young & Thompson

[57] ABSTRACT

A method and apparatus for stimulating a heart to eliminate rhythmic abnormalities, especially tachycardias. In accordance with a method of orthorhythmic stimulation, the electric stimulation is applied after a delay period following a natural electrosystole. The electric stimulation comprises a train of pulses, preferably between three and twenty, which straddles the end of the delay period. Such trains of pulses may also alternate with one or more trains of a single pulse. The stimulator comprises a trigger responsive to the natural electrosystole of the heart, a first counter of predetermined frequency and a second counter of adjustable higher frequency serially connected to the first counter for driving a pulse generator generating the trains of pulses.

11 Claims, 6 Drawing Figures

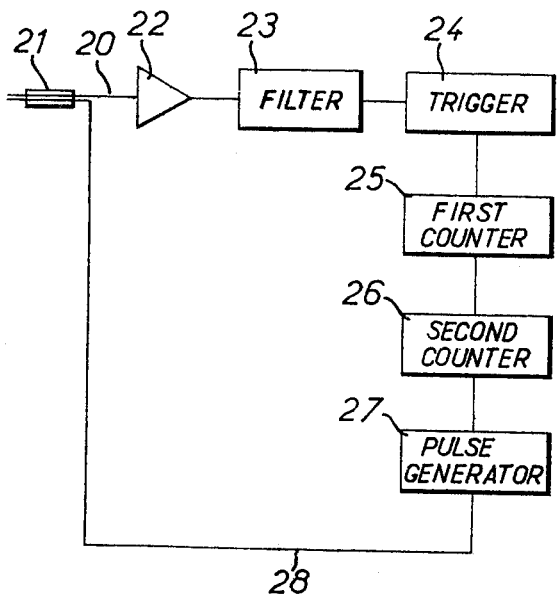
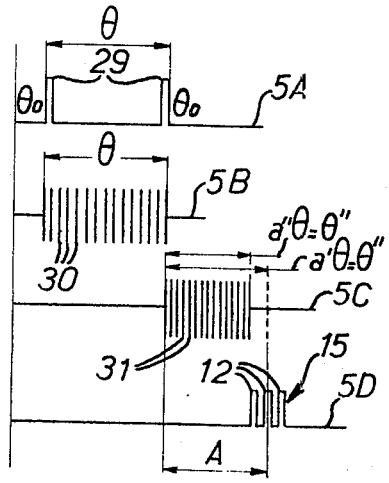
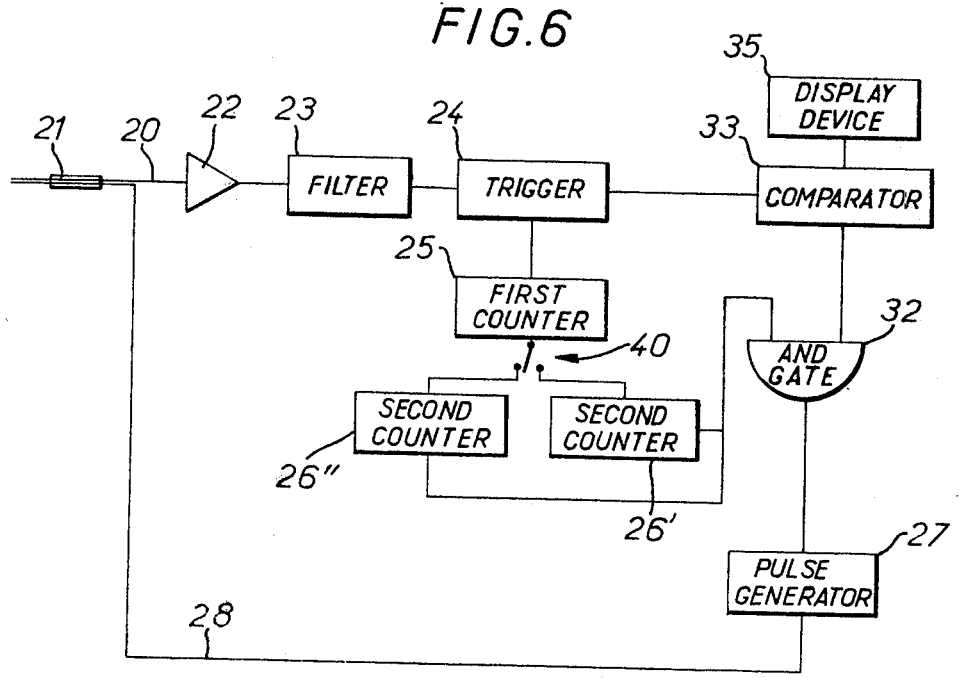

3,939,844

METHOD AND APPARATUS FOR STIMULATING A HEART TO ELIMINATE RHYTHMIC ABNORMALITIES, ESPECIALLY TACHYCARDIAS

FIELD OF THE INVENTION

The present invention relates generally to electric stimulation of the heart of a person afflicted with rhythmic abnormalities, and more particularly, but not exclusively, with the speed-up of the heart beat known as tachycardia.

BACKGROUND OF THE INVENTION

As is known, numerous tachycardial arrhythmias may be reduced instantaneously by the electric stimulation of the heart provided that the stimulation is delivered within a narrow zone of the cardiac cycle called the effective zone.

It has been found that the location of effective zone in the cardiac cycle, as well as the duration per se of the effective zone, varies markedly from one cardiac cycle to another mainly in accordance with the duration of the preceding cardiac cycle called the R—R interval (the interval between consecutive R's); in general, the shorter the duration of the preceding cardiac cycle, the closer the effective zone comes to the beginning of the cycle, with a corresponding reduction in its own length.

Further, according to a method called orthorhythmic stimulation with automatically variable hysteresis, it has been proposed to make the delivery of the electric stimulation pulse dependent upon the duration of the preceding cardiac cycle with a view to ensuring the delivery of the pulse inside the effective zone of the instant cardiac cycle; in practice, and according to the method, the application of the desired electric stimulation of the heart is effected after a period of time called the delay period, which, counting from the natural electrosystole triggering the stimulation, is variable as a function of the duration of the preceding cardiac cycle.

The term "natural electrosystole" is used throughout the present specification as meaning the electrical expression of a natural or induced systole, i.e. the mechanical contraction of the heart.

Yet there may be large and abrupt variations in frequency of the tachycardial arrhythmia treated-namely, when the patient undergoes an intensive drug treatment at the same time. In this case, the effective zone of the cardiac cycle may be sufficiently shortened and-/or sufficiently displaced so that, despite the correction provided by the method of orthorhythmic stimulation with automatically variable hysteresis, the stimulation pulse falls outside the effective zone.

Consequently, the stimulation pulse is not able to alleviate cardiac arrhythmias; on the contrary, such a stimulation pulse is capable of provoking an additional contraction of the heart thereby accelerating the heart beat.

SUMMARY OF THE INVENTION

The general objects of the present invention are the provision of a method and apparatus for overcoming these drawbacks.

The method according to the invention is of the type in which the electric rhythm of a patient's heart is monitored, and in case of an abnormality, electric stimulation is applied to the heart muscle after a delay period which, counting from the natural electrosystole of the heart muscle triggering the stimulation, is variable as a function of the duration of the cardiac cycle immediately preceding said electrosystole, wherein the improvement comprises, for at least one of the electrosystoles triggering stimulation, said stimulation comprising a train of $n$ consecutive stimulation pulses, $n$ being greater than two, the length of the pulse train being chosen to straddle the end of the delay period.

The train of pulses according to the invention permits the straddling of an optimum point in the cardiac cycle, as previously determined by the method of orthorhythmic stimulation with automatically variable hysteresis, so that with all probability at least one of the pulses of the train falls in the particular effective zone desired.

It has already been proposed to apply to a patient's heart an electric stimulation in the form of a train of consecutive pulses, but up to now such stimuli were delivered in response to a single natural electrosystole after a constant coupling interval or period and only at the auricles of the heart.

The present invention provides only one short stimulation train applied to the heart because the point in time of application in the cardiac cycle is already more precisely located in the R—R interval by the orthorhythmic method which permits application at the ventricles of the heart, this electric stimulation being particularly effective owing to the fact that it is delivered at the precise moment, as indicated above.

BRIEF DESCRIPTION OF THE DRAWINGS

The features and advantages of the invention will be more apparent from the description which follows, given by way of example, with reference to the accompanying schematic drawings, in which:

FIG. 4 shows a block diagram of the electric stimulation apparatus or stimulator according to the invention;

FIG. 5 shows a diagram illustrating the operation of the apparatus; and

FIG. 6 is a block diagram similar to that of FIG. 4 for an alternative embodiment of the electric stimulator according to the invention.

DETAILED DESCRIPTION OF THE STATE OF THE ART

Figure 1:
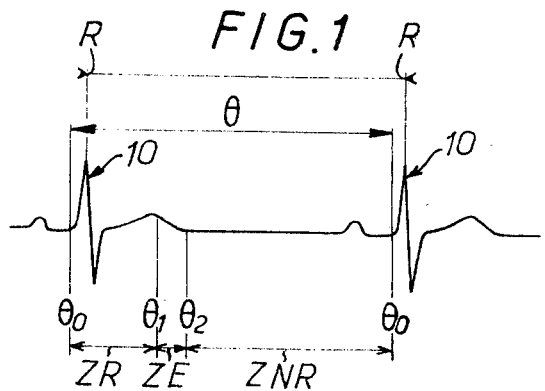
FIG. 1 illustrates the electrocardiogram of a normal person.

It is possible, as is known, to distinguish in a person's electric cardiac cycle having a period $\theta$ three distinct consecutive zones; these zones are schematically illustrated in FIG. 1 in which the R—R interval is also shown.

Starting from the origin $\theta_o$ of an electrosystole 10 there is first of all a zone ZR called the refractory zone during which the application of any electric stimulation on the heart muscle is without effect.

Then, starting from a point in time $\theta_1$ which marks the end of the refractory zone ZR, there is a second zone ZE called the effective zone.

The effective zone is relatively short, its duration is between about 15 milliseconds and about 100 milliseconds depending, namely, on the individual and the possible pathological condition of the speeded up heart muscle.

Finally, after the point $\theta_2$ marking the end of the effective zone ZE there is a third zone ZNR called the nonrefractory zone during which the application of an electric stimulation on the heart muscle is capable of provoking its contraction.

The refractory zone ZNR ends with the appearance of a new electrosystole 10 marking the beginning of another electric cardiac cycle.

It is also known that in the case of a rhythmic abnormality of the tachycardia type, it is possible to bring the rhythm back to normal, and in rarer cases it is possible to slow the rhythm of the heart by continuous stimulation, applying an electric stimulation to the heart muscle at the auricles or the ventricles, provided that the electric stimulation occurs precisely during the effective zone defined hereinabove.

Figure 2:
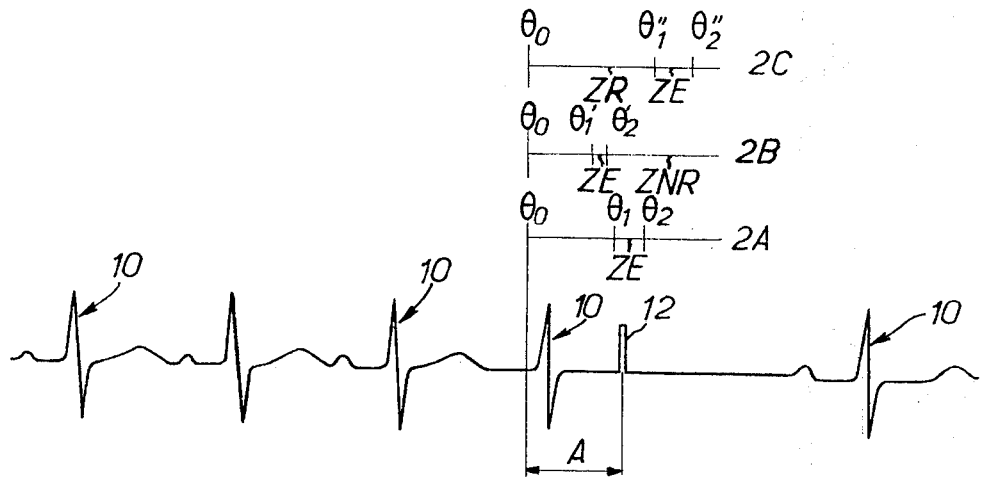
FIG. 2 illustrates an electrocardiogram of a person having a tachycardial abnormality and for which conventional electrical stimuli are applied to the patient's heart.

In practice, and as shown in FIG. 2, the application of such an electric stimulation is effected at the present time by means of a single pulse 12; this pulse is applied to the heart muscle after a delay period A starting from the origin $\theta_o$ of the natural electrosystole 10 which, occuring prematurely, electronically triggers the detection of a rhythm abnormality and applies an electric stimulation.

Now, as mentioned above, the duration $\theta_1 - \theta_2$ of the effective zone ZE is very short.

If the stimulation pulse 12 falls exactly in the effective zone ZE which is the case for the line 2A in FIG. 2, it is possible, as illustrated, to bring the heart back to normal electric rhythm.

If, on the other hand, as indicated in line 2B, a large increase in the tachycardial abnormality brings about concomitantly a reduction in the duration of the effective zone ZE, now $\theta'_1 - \theta'_2$ and a reduction of the time $\theta_o - \theta'_1$ separating the origin of the effective zone from the origin of the preceding natural electrosystole 10, the electric stimulation pulse 12 then falls in the nonrefractory zone ZNR and is no longer capable of ensuring a return to the normal heart rhythm, but, on the contrary, may accelerate the heart rhythm.

Finally, if an abrupt slowdown of the heart rhythm simultaneously brings about, as shown on line 2C in FIG. 2, an increase of the duration $\theta_o - \theta''_1$ between the origin of the effective zone ZE and the origin of the preceding natural electrosystole 10 with a possible concomitant increase in the duration $\theta''_1 - \theta''_2$ of the effective zone, the stimulation pulse 12 falls in the refractory zone ZR and is ineffective.

DETAILED DESCRIPTION OF THE PREFERRED EMBODIMENTS

According to the invention, and for at least one of the electrosystoles 10 triggering the stimulation, the stimulation is effected, not by means of a single pulse 12, but by means of a train 15 of successive pulses, the number $n$ of pulses in the train 15 being greater than two and the time length E of the train 15 being effectivelly chosen so that the train straddles the normal end of the delay period A.

Figure 3:
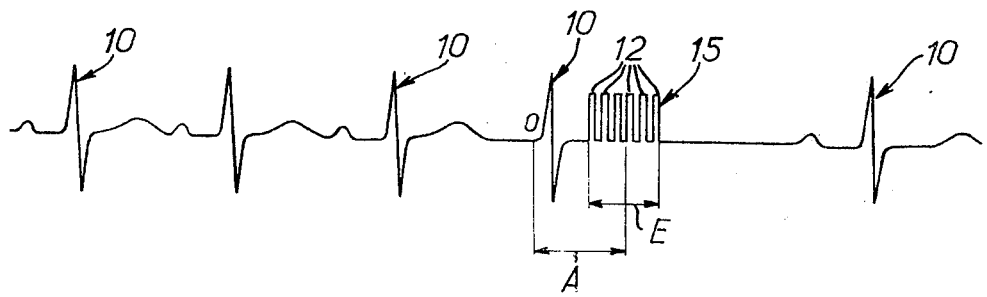
FIG. 3 is similar to FIG. 2 and illustrates the application of electric stimulation to the patient's heart according to the invention.

In other words, and as shown in FIG. 3, the first pulse of the train 15 preferably occurs before the end of the delay period A, and the last pulse 12 of the train 15 preferably occurs after the end of the delay period.

In the illustrated example, the pulses of the train 15 according to the invention are identical in shape and duration and are of constant frequency.

It goes without saying that, alternatively, the pulses 12 of a train of pulses 15 may be of different shape, and/or duration, and/or frequency, for example, the pulses may be in increasing or decreasing order of frequency.

By way of nonlimiting example, the pulse train 15 preferably comprises a number $n$ of pulses 12 between three and twenty, each of the pulses 12 being rectangular and having a duration of 1 millisecond and an amplitude in the order of 0.5 to 6 volts, and each pulse 12 being separated from the next pulse by a free interval of between 2 and 10 milliseconds.

As shown in FIG. 4, a stimulator apparatus according to the invention generally comprises a probe wire 20 which when placed in a catheter 21, is adapted to detect the electrical activity in the auricle or the ventricle of a person's heart.

The probe wire 20 is connected to the input lead of an amplifier 22 with a feedback loop (not shown) which permits, in a known manner, level control.

The output of the amplifier 22 is connected to a trigger 24, for example a Schmitt trigger, by means of a filter 23 adapted to eliminate the effects of possible interference.

The trigger 24 controls a first clock signal counter 25 having a predetermined frequency F which, in turn, controls a second clock signal counter 26 having an adjustable frequency F'' which is chosen greater than the frequency F of the first clock signal counter 25.

The second clock signal counter 26 controls, in turn, a pulse generator 27; the output of the pulse generator is connected to a stimulation conductor 28 which, together with the probe wire, 20, is arranged in the catheter 21 for introduction into the auricle and/or ventricle of the heart to be stimulated.

A voltage signal 29 is thus present after each electrosystole.

From each voltage signal 29 to the following voltage signal the clock signal counter 25 records the number $n$ of frequency F pulses.

The end of the count of the first clock signal counter 25 marks the beginning of the count of the second clock signal counter 26. The second clock signal counter 26 counts during its operative period a number N of pulses 31 equal to the number of pulses 30 initially recorded by the first clock signal counter 25.

However, since the frequency F'' of the second clock signal counter 26 is greater than the frequency F of the first clock signal counter 25, the counting period $\theta''$ of the second clock signal counter 26 is less than the counting period $\theta$ the first clock signal counter 25 corresponding to the period of the detected cardiac cycle.

Since, in accordance with the known method of orthorythmic stimulation, we are dealing with a single stimulation pulse produced after a delay period A, the frequency of the second clock signal counter 26 is adjusted to a value F' so that the duration of the corresponding counting period $\theta'$ is a fraction $a'\theta$ of the period of the cardiac cycle equal to the delay period A.

Preferably, the second clock signal counter 26 is adjusted to an even higher frequency F'', selected so that the corresponding counting period $\theta''$ is a fraction $a''\theta$ of the period $\theta$ of the cardiac cycle less than the fraction $a'\theta$ corresponding to the delay period A.

For this reason, the pulse generator 27 is turned on before the end of the delay period A defined above.

The pulse generator 27 is adjusted so as to emit a train 15 of pulses from the end of the counting phase of the second clock signal counter 26 up to a predetermined time period after the delay period A.

The construction of such a pulse generator as well as other components of the stimulator apparatus is known per se and within the skills of the man in the art. Their construction will therefore not be described in detail here.

It is also within the skills of the man in the art to ensure the possibility of manually or automatically adjusting the shape and/or the duration and/or the frequency of the pulses 12 of the pulse train 15 furnished by the pulse generator 27.

From the above, an electric stimulation is systematically delivered by the stimulation conductor 28 during each electric cycle of the heart.

According to the alternative embodiment shown in FIG. 6 and as is known per se, such stimulations are only supplied in case of necessity, i.e., only when the monitored electric cycle is higher than a predetermined reference value.

In addition, according to this embodiment, two second clock signal counters 26', 26" with adjustable frequencies are arranged in parallel and connected at the output end of the first clock signal/counter 25 and selected by a selection switch 40.

As above, the first clock signal counter 25 is adjusted to the frequency F" greater than the frequency F' corresponding to the delivery of a single stimulation pulse after a delay period A.

One of the second clock signal counters 26', 26" on the other hand is adjusted to the frequency F' which is also greater than the frequency F of the first clock signal counter 25.

The output leads of the second clock signal counters 26' and 26" are connected in parallel to one of the input leads of an AND gate 32, the other input lead of which carries the output of the frequency comparator 33 which is connected to the output of the trigger 24 and to the display device showing the predetermined reference frequency.

The selection switch 40 determines which of the second clock signal counters 26' and 26" is to be put into operation depending on whether the electric stimulation to be applied is to consist of a single pulse, as is conventional, or a train of pulses as described above.

In any case the application of electric stimulation is produced according to FIG. 6 only when the comparator 33 has detected a speed up in the frequency of the heart cycle with respect to the reference frequency shown on the display device.

By means of the selection switch, it is possible to alternate a single pulse cardiac stimulation, possibly repeated during several cardiac cycles, with a cardiac stimulation formed as a train of pulses which may also be repeated over several cardiac cycles; the permutations of one type of stimulation with another may even be programmed automatically.

Although the present method and apparatus have been described with respect to human beings it is clearly applicable to the hearts of mammals, in general.

The present invention is, of course, not limited to the embodiments described and illustrated herein nor the particular modes of carrying out the invention described, but includes, on the contrary, all modifications and variations within the scope of the appended claims.

What I claim is:

1. A method of electrically stimulating a heart, comprising monitoring the heart for rhythmic abnormalities, measuring the duration of a first cardiac cycle immediately preceding a second cardiac cycle during which the heart is to be electrically stimulated, determining a delay period as a function of the said first cardiac cycle, generating a train of $n$ consecutive stimulation pulses, $n$ being greater than two, so that the train of $n$ pulses straddles the end of the delay period running from the natural electrosystole at the beginning of said second cardiac cycle, and applying said train of $n$ pulses to the heart.

2. A method according to claim 1, further comprising alternating at least one said train of $n$ successive stimulation pulses with at least one train of a single electric stimulation pulse.

3. A method according to claim 1, wherein the duration of the pulses of a given train is variable.

4. A method according to claim 1, wherein the shape of the pulses of a given train of pulses is variable.

5. A method according to claim 1, wherein the frequency of the pulses of a given train of pulses is variable.

6. A method according to claim 1, wherein the pulses of a given train are identical and of constant frequency.

7. A method of electrically stimulating a heart, comprising monitoring the heart for rhythmic abnormalities, measuring the duration of a first cardiac cycle immediately preceding a second cardiac cycle during which the heart is to be electrically stimulated, determining a delay period as a function of the first cardiac cycle, generating a train of more than two consecutive rectangular stimulation pulses each having a duration of about one millisecond and an amplitude in the order of 0.5 to 6.0 volts, the train of $n$ pulses straddling the end of the delay period running from the natural electrosystole at the beginning of said second cardiac cycle, and applying said train of $n$ pulses to the heart.

8. A method as claimed in claim 7, the pulses of said train being separated from one another by free intervals between 2 and 10 milliseconds.

9. Apparatus for electric stimulating of a heart muscle, comprising a probe wire for monitoring the electric activity of the heart muscle, a trigger operatively connected to the probe wire, a first clock signal counter having a predetermined frequency F, a second clock counter having an adjustable frequency F" greater than F driven by the first clock counter, a pulse generator driven by the second clock counter, and a stimulation conductor connected to the pulse generator adapted to be applied to the patient.

10. Apparatus according to claim 9, wherein there are two second clock counters having adjustable frequencies F' and F" resepectively greater than the frequency F of the first clock counter, said second clock counters being arranged in parallel, a selection switch being provided for selecting one of said second clock counters.

11. Apparatus according to claim 10, further comprising an AND gate connected between the second clock counters and the pulse generator, a comparator connected to a trigger and a display device, the outlet of said comparator being connected to an input of the AND gate.

* * * * *